United States Patent
Watkins (10) Patent No.: US 6,536,746 B2
(45) Date of Patent: Mar. 25, 2003

(54) METHODS AND APPARATUS FOR LOCALIZED DELIVERY OF SCENTED AEROSOLS

(75) Inventor: Carl J. Watkins, Eugene, OR (US)

(73) Assignee: MicroScent LLC, Menlo Park, CA (US)

( * ) Notice: Subject to any disclaimer, the term of this patent is extended or adjusted under 35 U.S.C. 154(b) by 0 days.

(21) Appl. No.: 10/000,432

(22) Filed: Nov. 30, 2001

(65) Prior Publication Data

US 2002/0036358 A1 Mar. 28, 2002

Related U.S. Application Data

(62) Division of application No. 09/522,977, filed on Mar. 10, 2000.
(60) Provisional application No. 60/123,970, filed on Mar. 12, 1999.

(51) Int. Cl.$^7$ .................................................. B01F 3/04
(52) U.S. Cl. ...................... 261/26; 261/30; 261/78.2; 261/81; 261/DIG. 65; 261/DIG. 88; 96/27; 96/222; 422/124
(58) Field of Search ........................... 261/26, 30, 78.2, 261/81, DIG. 65, DIG. 88; 96/27, 222; 422/124, 125; 239/44

(56) References Cited

U.S. PATENT DOCUMENTS

| | | | |
|---|---|---|---|
| 2,207,889 A | * | 7/1940 | Kingman .................... 422/125 |
| 2,540,144 A | | 2/1951 | Stern |
| 2,562,960 A | | 8/1951 | Stern |
| 2,686,944 A | | 8/1954 | Gubelin |
| 2,813,452 A | | 11/1957 | Laube |
| 2,905,049 A | | 9/1959 | Laube |
| 3,050,870 A | | 8/1962 | Heilig |
| 3,795,438 A | | 3/1974 | Westenholz et al. |
| 3,804,592 A | | 4/1974 | Garbe |
| 4,229,415 A | | 10/1980 | Bryson |

(List continued on next page.)

FOREIGN PATENT DOCUMENTS

| | | |
|---|---|---|
| DE | 4033076 | 4/1992 |
| DE | 4135796 | 5/1993 |
| DE | 19626602 | 4/1997 |
| JP | 64-5556 | 1/1989 |

OTHER PUBLICATIONS

Jacobson, L., "Picking up the scent of a new web technology," *The Washington Post* (Nov. 22, 1999) p. A11.

Primary Examiner—Robert A. Hopkins
(74) Attorney, Agent, or Firm—Townsend and Townsend and Crew LLP (57) ABSTRACT

The present invention provides systems and methods for delivering a controlled amount of scent to a target user. Such methods and systems will preferably provide carefully direct boluses or streams of scent(s) to a single or small group of individual(s) using a bolus generator so as to avoid cross-contamination of scents with other persons and other locations. The present invention preferably delivers the bolus of scent as an air ring. The scented air ring moves through the air between the scent generating device directly to the user as a cohesive unit of air. This phenomenon is similar to a "smoke ring" exhaled by a smoker. The scent ring can be directed with accuracy to a localized target as small as the nose of a single user, such that the entire dosage can be delivered to only the user's direct vicinity. Such targeted delivery minimizes the amount of scent that must be delivered to achieve a desired level of scenting at the target location. Advantageously, the amount of scent that must be removed or dissipated from the user's area is also reduced. In another aspect, the present invention provides anti contamination devices that inhibit the contamination of the sequential delivery of scent chemicals.

29 Claims, 12 Drawing Sheets

U.S. PATENT DOCUMENTS

| | | |
|---|---|---|
| 4,385,814 A | 5/1983 | Elliot |
| 4,556,539 A | 12/1985 | Spector |
| 4,562,510 A | 12/1985 | Forry et al. |
| 4,603,030 A | 7/1986 | McCarthy |
| 4,629,604 A | 12/1986 | Spector |
| 4,735,282 A | 4/1988 | Lippold |
| 4,952,024 A | 8/1990 | Gale |
| 5,011,632 A | 4/1991 | Yano et al. |
| 5,023,020 A | 6/1991 | Machida et al. |
| 5,069,876 A | 12/1991 | Oshinsky |
| 5,105,133 A | 4/1992 | Yang |
| 5,171,485 A | 12/1992 | Ryan |
| 5,297,988 A | 3/1994 | Nishino et al. |
| 5,318,503 A | 6/1994 | Lord |
| 5,398,070 A | 3/1995 | Lee |
| 5,565,148 A | 10/1996 | Pendergrass, Jr. |
| 5,591,409 A | 1/1997 | Watkins |
| 5,610,674 A | 3/1997 | Martin |
| 5,635,229 A * | 6/1997 | Ray .................... 206/205 |
| 5,724,256 A | 3/1998 | Lee et al. |
| 5,735,918 A | 4/1998 | Barradas |
| 5,760,873 A | 6/1998 | Wittek |
| 5,785,204 A | 7/1998 | Thompson et al. |
| 5,797,898 A | 8/1998 | Santini, Jr. et al. |
| 5,823,434 A | 10/1998 | Cooper |
| 5,949,522 A | 9/1999 | Manne |
| 5,972,290 A | 10/1999 | De Sousa |
| 6,024,783 A | 2/2000 | Budman |
| 6,152,829 A | 11/2000 | Jaidka et al. |
| 6,357,726 B1 | 3/2002 | Watkins |
| 6,371,450 B1 * | 4/2002 | Davis et al. .................. 261/104 |

* cited by examiner

METHODS AND APPARATUS FOR LOCALIZED DELIVERY OF SCENTED AEROSOLS

CROSS-REFERENCES TO RELATED APPLICATIONS

This application is a division of, and claims the benefit of application Ser. No. 09/522,977, filed Mar. 10, 2000, which claims the benefit of provisional application no. 60/123,970, filed Mar. 12, 1999, under 37 C.F.R. §1.78, the full disclosure of which is incorporated herein by reference.

BACKGROUND OF THE INVENTION

The present invention relates generally to the delivery of chemicals, and more particularly to methods and systems for the controlled delivery of scented aerosols to a localized target.

The addition of scent to entertainment or other activities connected with data or information dissemination is known. Increased use of computers, game consoles, internet appliances, and other individual oriented devices have brought about an increased desire to synchronize the delivery of scents in conjunction with these and other automated activities. The human olfactory senses are very sensitive and the accuracy and consistency of the scent is critical. A major criteria of success is the ability to deliver scents to the user accurately, quickly, and cleanly without impacting other people in the vicinity.

Most conventional systems involve use of a fan that blows scented chemicals in the direction of the target user. Unfortunately, the conventional devices lack the means to control the delivery of the scent to the specific target and often fill the entire room with large amounts of the scent chemical. Because of the nature of the scented oils and chemicals, it is often difficult to remove the scent chemicals prior to the introduction of a new scent. Consequently, the ensuing deliveries of different scents are often contaminated with the lingering scent of the previously delivered scent.

Therefore, as can be appreciated, there is a need of systems and methods which can provide an individualized scent experience while reducing the level of contamination of new scents with the lingering scent from the previous deliveries.

SUMMARY OF THE INVENTION

The present invention generally provides systems and methods for delivering a controlled amount of scent to a target user. Such methods and systems will preferably provide carefully direct boluses or streams of scent(s) to a single or small group of individual(s) so as to avoid cross-contamination of scents with other persons and other locations.

The present invention preferably delivers the bolus of scent as an air ring. The scented air ring moves through the air between the scent generating device directly to the user as a cohesive unit of air. This phenomenon is similar to a "smoke ring" exhaled by a smoker. The scent ring can be directed with accuracy to a localized target as small as the nose of a single user, such that the entire dosage can be delivered to only the user's direct vicinity. Such targeted delivery minimizes the amount of scent that must be delivered to achieve a desired level of scenting at the target location. Consequently, the amount of scent that must be removed or dissipated from the user's area is also reduced and the cross-contamination of the different scents is reduced.

Systems of the present invention typically have a plurality of storage chambers coupled to a venting chamber. An electrical signal generator and bolus generator, such as a vibratable diaphragm or an audio speaker, can be used to create a pulse to deliver the scent chemical. The electrical signal generator can be activated by mechanical means, an electronic signal embedded in a recorded media, an electrical signal generated by an interactive program, or the like. In most implementations, the electrical signal generator and bolus generator impart a rapid increase of air pressure in the venting chamber holding the scent. The delivery of the scent ring from the present invention is typically through an orifice or opening in the venting chamber. In most embodiments, the orifice can be aimed towards the direct vicinity of a user's nose, so as to maximize the scent experience to the target user. The size and speed of travel of the scent ring can be adjusted for different circumstances by changing the frequency and number of pulses, changing the size of the opening, the number of openings, or the like.

In another aspect of the present invention, a scent generating system can be configured to reduce the level of contamination of a new scent from the lingering scent of the previously delivered scent chemical. In some embodiments, an exhaust fan and air filter are used to remove the lingering scented air in the venting chambers. Optionally, air can be further be filtered while being drawn into the chamber to reduce the amount of contaminated air drawn into the venting chamber. Therefore, newly generated scents will contain only a limited amount of unwanted contaminants.

Because it is difficult to remove all of the scents retained in the venting chamber, some implementations of the present invention can have an absorptive material, such as an absorptive clay, positioned over at least a portion of the venting chamber. The absorptive material attracts the scent chemicals and absorbs them with a trapping effect so as to inhibit contamination of subsequent scent chemicals moved through the venting chamber.

As an alternative to the absorptive material, another method that can be used to reduce the contamination of subsequent scents is to impart a similar electrical charge to both the venting chamber and the scent chemicals. The two similarly charged elements repel each other and limit the adherence of the scent to the venting chamber.

The individual scent chemicals are each typically contained in a separate cartridge that is inserted into a receptacle inside the enclosure. At least one scent chemical is selected from the plurality of scent cartridges and it is moved to the venting chamber through a delivery system. In one implementation, the delivery system has a small pump that imparts a steady pressure into one opening of the cartridge. The steady pressure enters through a first one way check valve and creates an increase air pressure in the interior of the cartridge. A second check valve opens and allows scented air to be emitted into the venting chamber for delivery to the user. In most embodiments, an electrical signal controls the opening of a regulator valve that allows the flow of the air pressure through the check valves. In order to add further precautionary measures to minimize scent leakage, the cartridges can have a sealing o-ring encircling the outside which provides a frictionally adhered connection between the cartridge and the interior walls of the holding receptacle.

After being moved from the cartridges, the scent chemical, if in liquid form, may be vaporized using a variety of methods, such as flowing the scent chemical through a micro-pump or a nano-pump, saturating a porous membrane, or vaporizing a liquid using an electrically activated piezo-ceramic plate, a laser, or the like.

The control of the scent generating system is typically through the use of microprocessor circuitry which controls the timing and frequency of the emission. The control circuitry is typically linked to programmable electronic activation means through standard communication links, such as cables, wireless connection, infrared, radio, or the like.

In another aspect, the present invention provides a system for delivering scent chemicals. The system has a venting chamber having an orifice. A plurality of cartridges hold the individual chemicals. At least one of the cartridge can be activated to release its scent chemicals to the venting chamber. A bolus generator assembly is coupled to the venting chamber such that the bolus generator assembly delivers a pulse of air which forces a ring bolus of the chemical through the orifice in the venting chamber.

In another aspect, the present invention provides a system for delivering a scent chemical to a localized target. The system comprises a venting chamber having an orifice. A plurality of storage means store individual scent chemicals. The storage means control the release of at least one selected scent chemical into the venting chamber. Pulse means deliver a controlled air pulse to the scent chemical within the venting chamber to expel the scent chemical through the orifice in a shape of a ring bolus.

In still another aspect, the present invention provides a system for delivering scent chemicals to a localized target. The system has a venting chamber with an opening. The venting chamber is adapted to receive stream(s) of scent chemicals. A dispersion mechanism is in communication with the venting chamber such that the dispersion mechanism moves the scent chemical through the venting chamber. An absorptive liner is formed over at least a portion of the venting chamber to absorb the scent chemical remaining in the venting chamber after the scent chemical has been moved through the venting chamber.

In yet another aspect, the present invention provides a system for dispensing a scent. The system has means for electrically charging a scent chemical. A venting chamber for receiving the electrically charged scent chemical has a like-charge such that the venting chamber repels the scent chemical and lessens the contamination from the scent chemical. A delivery mechanism is configured to force the scent chemical through an opening in the venting chamber.

In another aspect, the present invention provides a method. A scent chemical is selected from a plurality of scent chemicals. A scent ring is formed and directed toward a user.

In still another aspect, the present invention provides a method for a localized delivery of scents. A scent chemical is selected from a plurality of scent chemicals. An air pulse is generated to controllably disperse the vapor from the venting chamber in the form of a ring bolus.

In yet another aspect, the present invention provides a method. A first scent chemical is moved through a venting chamber. At least a portion of the residue of the first scent chemical within the venting chamber is absorbed so as to inhibit the contamination of a second scent chemical moved through the venting chamber.

In another aspect, the present invention provides a method. An electrically charged scent chemical is moved into a venting chamber. A like charge is provided to the venting chamber such that the like-charged venting chamber substantially repels the scent chemical so as to inhibit the scent chemical from adhering to the wall.

Other objects, features, and advantages of the present invention will become apparent upon consideration of the following detailed description and the accompanying drawings, in which like reference designations represent like features throughout the figures.

DESCRIPTION OF THE SPECIFIC EMBODIMENTS

Figure 1:
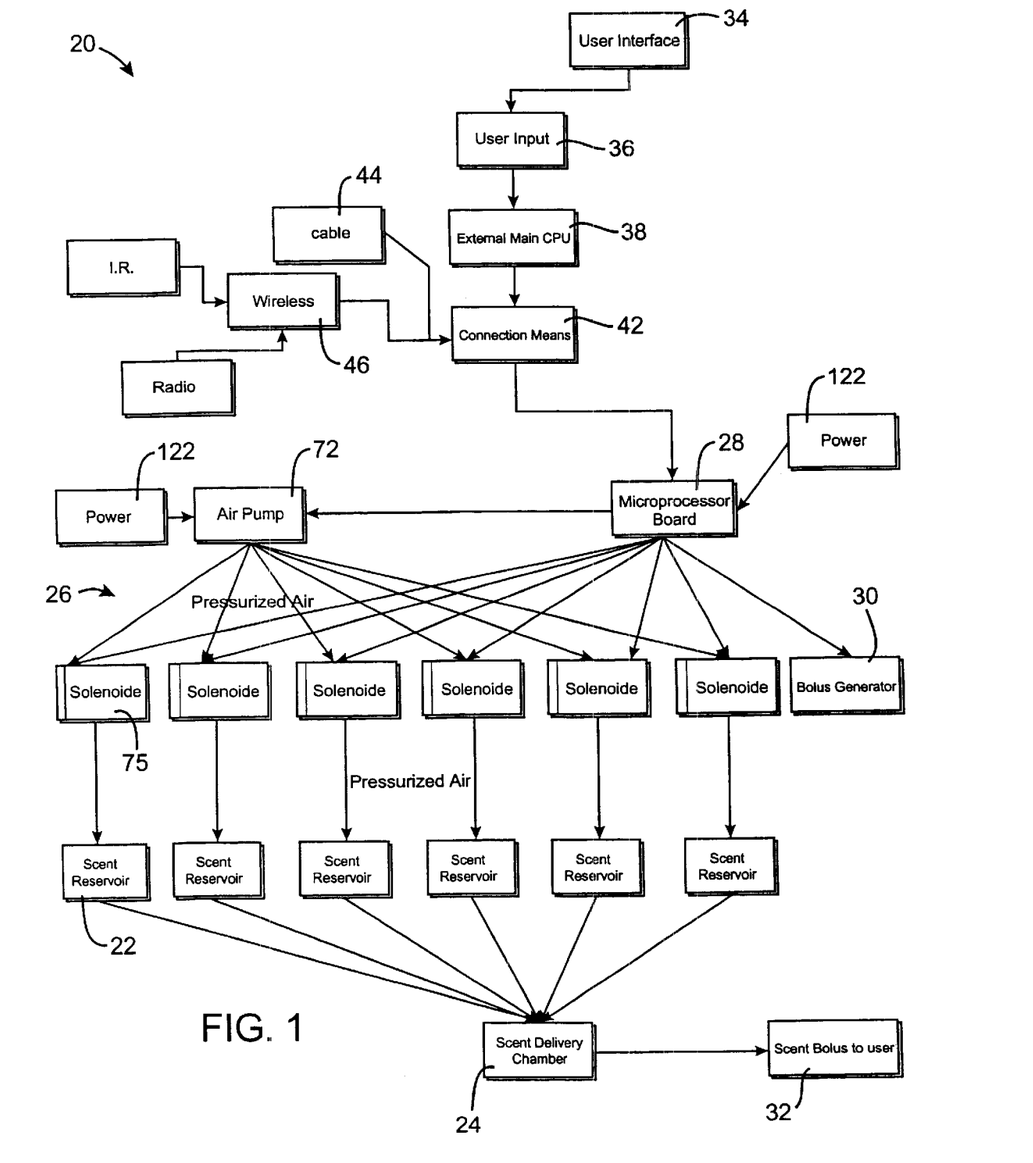
FIG. 1 is a simplified block diagram of one embodiment incorporating the present invention.
Figure 2:
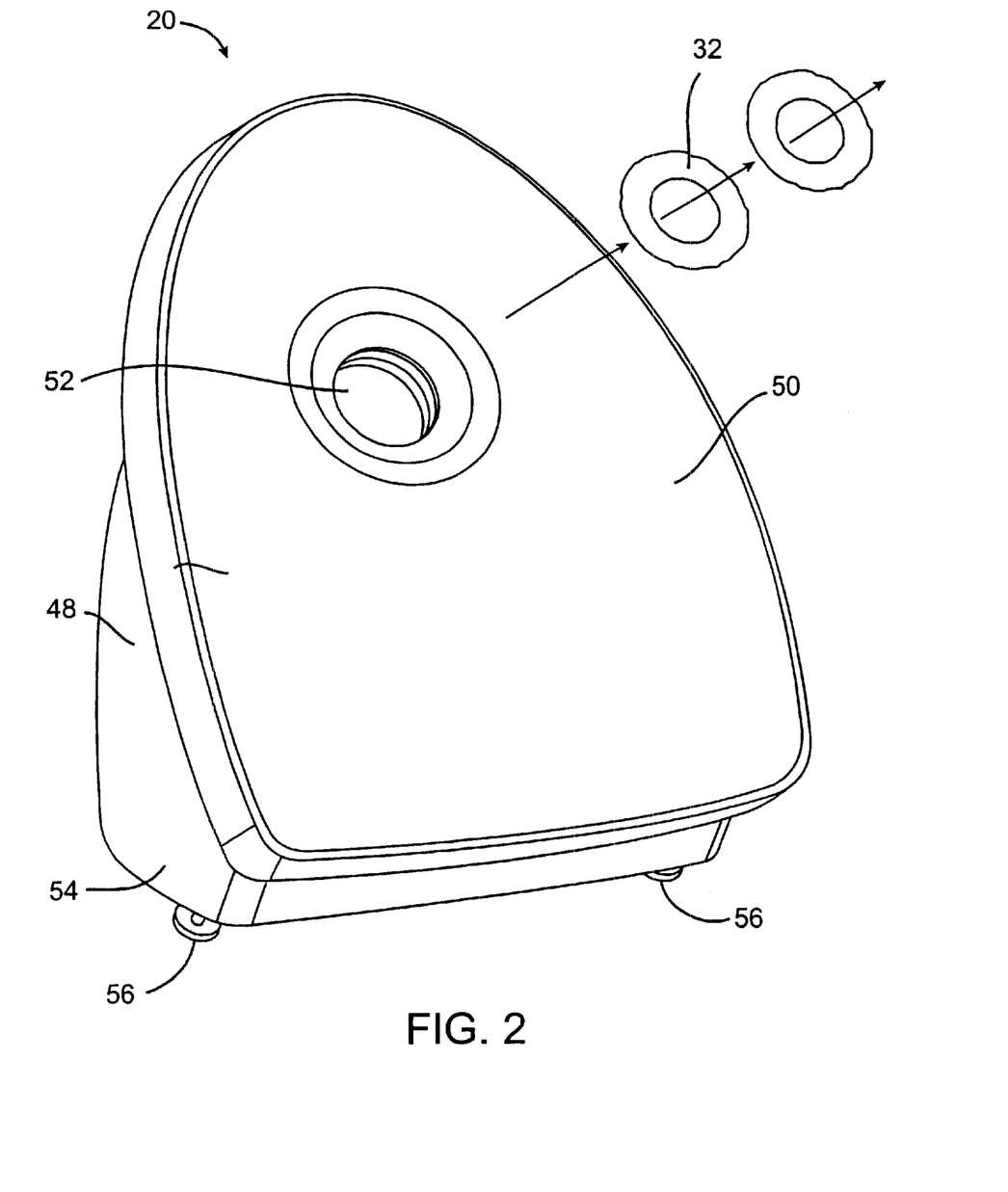
FIG. 2 is an isometric view of a scent generating system according to the present invention.

FIG. 1 shows a simplified block diagram of the components of a scent generating system 20 according to the present invention. The system generally includes a storage system 22, such as cartridges or reservoirs, that store individual scent chemicals. The storage system 22 is coupled to a scent venting chamber 24 through a delivery assembly 26. The delivery assembly 26 typically has some combination of valves, conduits, pumps, and vaporizers and can be configured to meter and control the flow of the scent chemicals from the cartridges 22 to the venting chamber 24. A signal from a control system 28 activates the delivery assembly 26 to move the selected scent chemical(s) from the selected cartridge(s) 22 to the venting chamber 24. Once the selected scent chemical(s) have been transferred to the venting chamber 24, a bolus generator 30, such as a vibratable diaphragm or a speaker, is activated by a signal generator (not shown) to generate an air pulse. The air pulse delivers the scent chemical through an orifice (not shown) in the venting chamber 24 and creates a ring bolus or scent ring 32 which can be controllably directed toward an individualized user.

An operator or user typically interacts with the scent generating system through a user interface 34 and user inputs 36. User inputs 36, such as buttons, levers, switches, joysticks, a keyboard, or the like, deliver a control signal through a CPU 38 to a microprocessor board 28 in the scent generating system 20. In most embodiments, the control signal can be transmitted through a connection interface 42 such as cable 44 or wireless connections 46 to activate the delivery of the scent chemical. As shown in FIG. 1, the user interface can be attached directly to the scent generating system or can be remotely connected to the scent generating system. It should be appreciated, however, that in other embodiments of the present invention, the scent generating system can be activated remotely through a network, such as the internet. In such embodiments, the user that receives the delivered scent would not have to interface directly with the interface 34 or user inputs 36.

The particular selection of the scent chemical and the sequence of the various selections over a period of time is controlled by the microprocessor board 28 and the CPU 38. The microprocessor may be pre-programmed to provide a prearranged sequence of scent chemicals when a pre-recorded presentation is playing, or the microprocessor board may be interactive and the scent delivery pattern will depend on the specific user inputs.

FIGS. 2–7 illustrate one exemplary embodiment of the scent generating system 20 of the present invention. The scent generating system 20 has a structural enclosure 48 which has a front panel 50, a base housing 54, and a directional orifice 52. The scent generating system 20 can be mounted on adjustable feet 56 to enable the direction of the scent ring to be aimed directly at the nose of the user. Removable cartridges 22 containing individual scented chemicals 58, chemical vapors 60, or both, are typically positioned in individual receptacles 62 in linear arrays of two or more such that at least a portion of the delivery assembly 26 is within the manifold 64 (FIGS. 3, 4, 7, and 8). A microprocessor board and/or electrical circuitry 28 are contained within the electronics housing 66 and can be accessed through a conventional data port 68. Thus, a user interface, user inputs, or a network connection can be connected to the microprocessor board 28 through the data port 68. The microprocessor board 28 is also electrically coupled to the delivery assembly 26 and the bolus generator 30 to coordinate the release and disbursement of the scent chemical 58, 60.

An exemplary storage system 22 is shown in FIGS. 1 and 8A to 8D. The cartridges can have a valve delivery assembly 26 to control the movement of the scent chemical to the venting chamber 24. The cartridge 22 includes an inner chamber 70 which holds the scent chemical 58 (and in some embodiments its vapor 60). In most embodiments, an air pump 72 can be used to deliver a continuous flow of air, a variable flow of air, or a pulsed flow of air through a conduit assembly 74 (FIG. 1). A solenoid regulator valve 75 is electrically coupled to the microprocessor board 28 and impedes the air flow to the cartridges 22. At least one of the solenoid regulator valves 75 can be opened in response to an electrical control signal from the microprocessor board 28 and the pressurized flow of air can enter the selected cartridge(s) 22 through an inferior check valve 76. After entering the chamber 70, the pressurized air will pick up the scent chemical 58, 60 and once the internal pressure of the cartridge chamber 70 reaches a pressure which can open a superior check valve 78, the air flow and scent chemical 58, 60 exit the cartridge through the superior check valve 78 and into the venting chamber 24. In one specific configuration, the scent chemical is stored in a liquid form within a sponge (not shown) in the cartridge. As the pressurized air passes through the sponge, the scent chemical 58 is moved directly to a vapor form as it is moved out of the cartridge. Other embodiments of solenoid-type valves are described in commonly owned U.S. Pat. No. 5,591,409, the full disclosure of which is incorporated herein by reference.

Figure 8A:
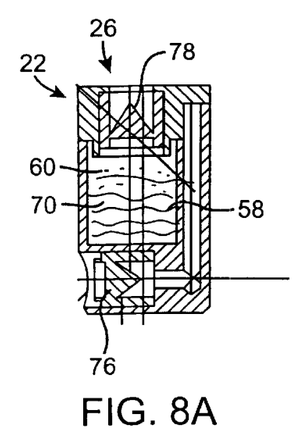
FIG. 8A is a cross sectional view of the cartridge.

When no air is flowing through the check valves 76, 78, the valves have a closing strength that is strong enough to prevent the scent chemical 58, 60 from escaping from the cartridges. Moreover, both the inferior check valve 76 and superior check valve 78 are preferably one way low-pressure valves that do not allow back flow through the valves.

Figure 6:
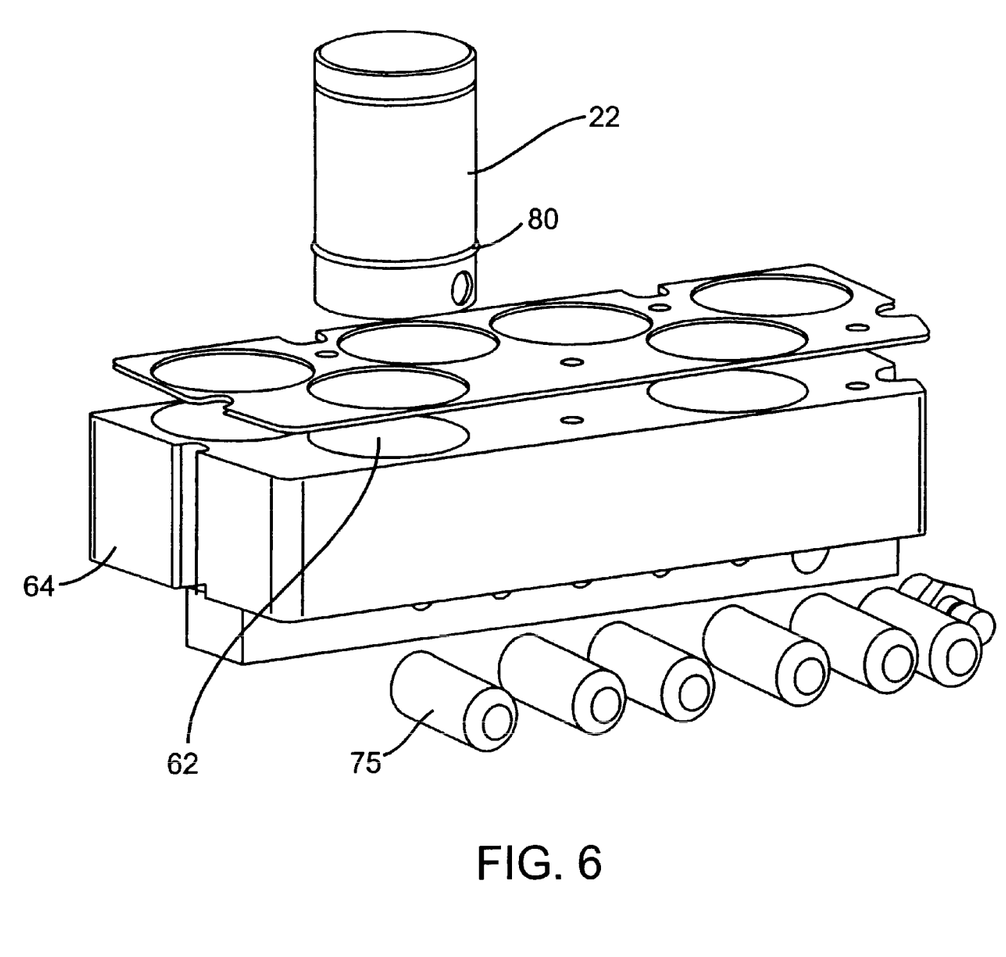
FIG. 6 is an exploded view of the cartridge manifold assembly.
Figure 7:
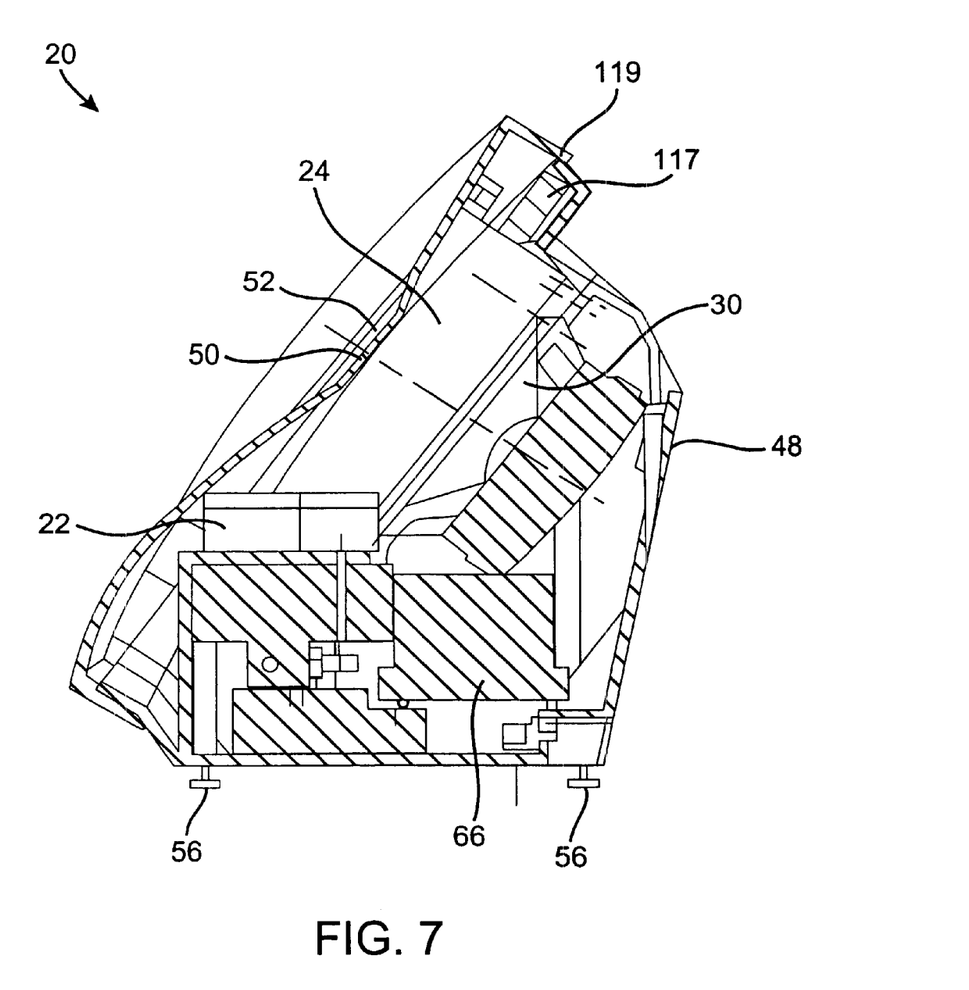
FIG. 7 is a cross-sectional view of the system of FIG. 2.
Figure 8B:
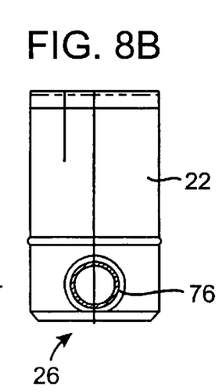
FIG. 8B is a side view of the cartridge.
Figure 8C:
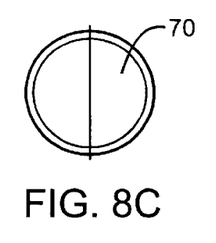
FIG. 8C is a top view of the cartridge.
Figure 8D:
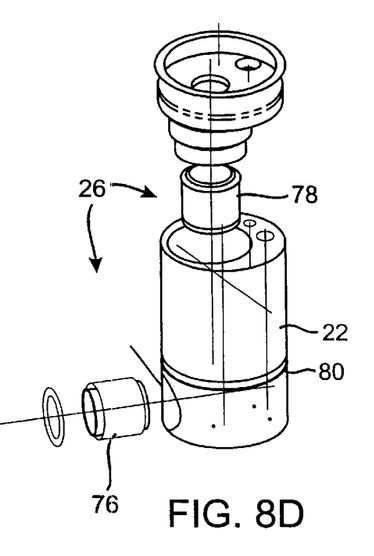
FIG. 8D is an exploded perspective view of the cartridge.

As shown in FIGS. 6, 8B, and 8D, in some implementations a rubber sealing ring 80 circles the scent cartridge 22 so that when the cartridge is inserted into the receptacle 62, a secure seal is created between the cartridge and the receptacle 62. The seal prevents air pressure at the base of the cartridge from leaking and further prevents the scent chemical in the cartridges 22 from escaping into the atmosphere and into the venting chamber.

Figure 9A:
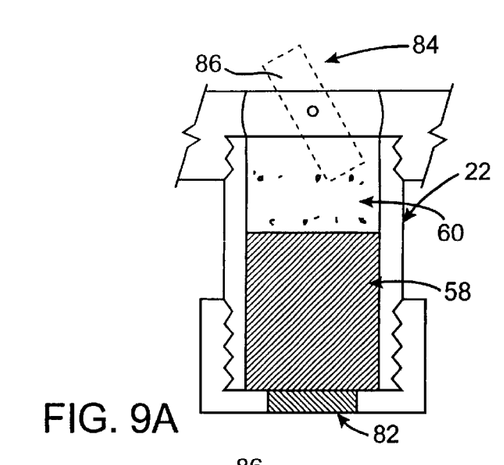
FIG. 9A is a cross sectional view of a cartridge having a piezo electric mechanism.
Figure 9B:
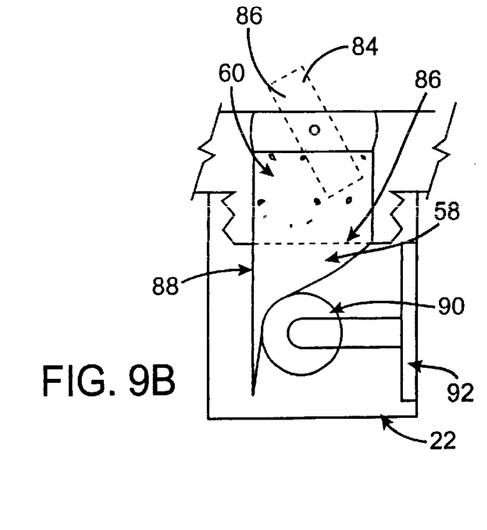
FIG. 9B is a cross sectional view of another embodiment of a cartridge having a piezo electric mechanism.
Figure 9C:
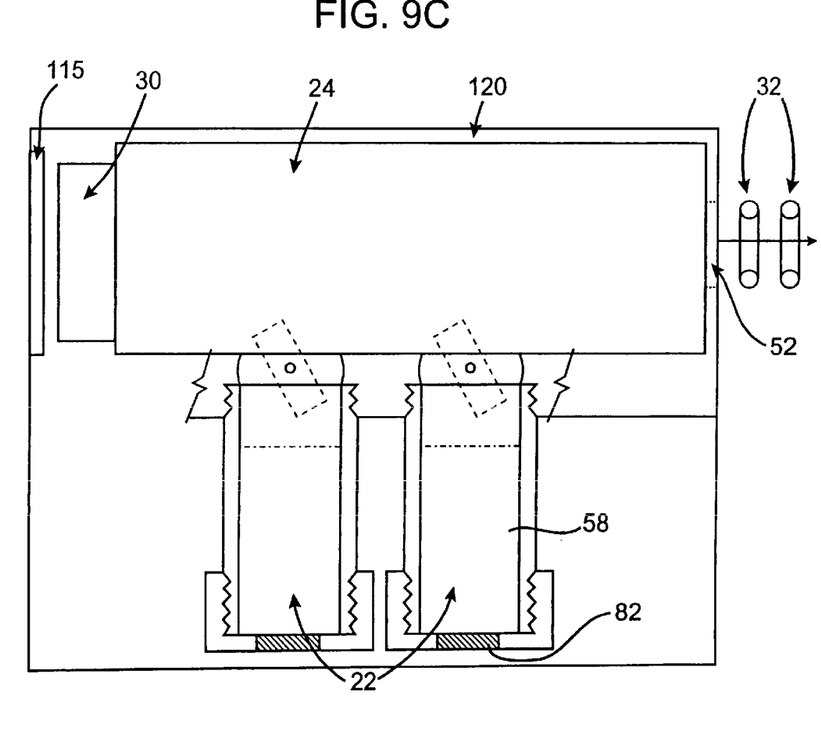
FIG. 9C is a cross sectional view of the scent generating system having the piezo electric mechanism.

Another exemplary scent generating system is illustrated in FIGS. 9A to 9C. This embodiment of the scent generating system 20 includes a plurality of cartridges 22 that are attached to piezo-electric mechanisms that cause the liquid scent chemical to vaporize when an electric charge is applied to the piezo-electric mechanism. The vaporized scent liquid can then be transferred to the venting chamber through a revolving delivery door assembly.

As shown in the embodiment of FIGS. 9A and 9C, the cartridge assembly 22 has a piezo electric ultrasonic nebulizer 82 that is continuously in contact with the scent chemical 58. Delivery of an electric charge through the nebulizer sublimates the scent liquid 58 into a gas vapor 60 which rises above the liquid chemical 58. After a sufficient quantity of the scent vapor 60 has been collected, a revolving delivery door 84 can be activated and rotated 180 degrees to receive the vapor 60 in a collection chamber 86. After the vapor 60 has been collected, the door is rotated another 180 degrees such that the measured quantity of scent vapor 60 is moved into the venting chamber 24. As above, once the scent vapor 60 has been delivered into the venting chamber 24, a signal causes the bolus generator 30 to vibrate in a series of pulses, each of which can force a scent ring 32 of gaseous vapor to be expelled through the orifice 52 at the end of the venting chamber 24. The scent rings 32 are directed at the general vicinity of the user's face, and more particularly at the user's nose.

In an alternative embodiment shown in FIG. 9B, a piezoceramic vibration plate 86 having holes can be attached near the top of the scent chemical 58 to sublimate the scent liquid into a vapor. The liquid scent chemical can be continuously in contact with the plate 86, or individual droplets can be applied through a wicking method, an elastomer funnel, or by some other droplet placing means. In the specific implementation shown, a blister pack 88 can be used to contain the scent chemical. Constant pressure with a moveable roller 90 within a track 92 forces the scent chemical into contact with the piezo electric vibration plate 86. As the scent chemical is vaporized, the moveable roller 90 can be moved upward to maintain contact between the scent chemical and the piezo-electric vibration plate 86. Similar to the embodiment of FIG. 9A, the revolving door assembly 84 or other delivery assemblies can then be used to deliver the vapor into the venting chamber 24.

Figure 10A:
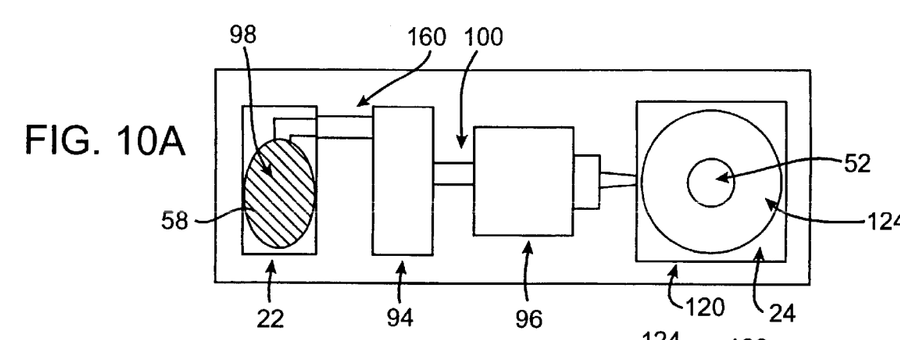
FIG. 10A is a cross sectional view of a system having a micro pump and a vaporizer.
Figure 10B:
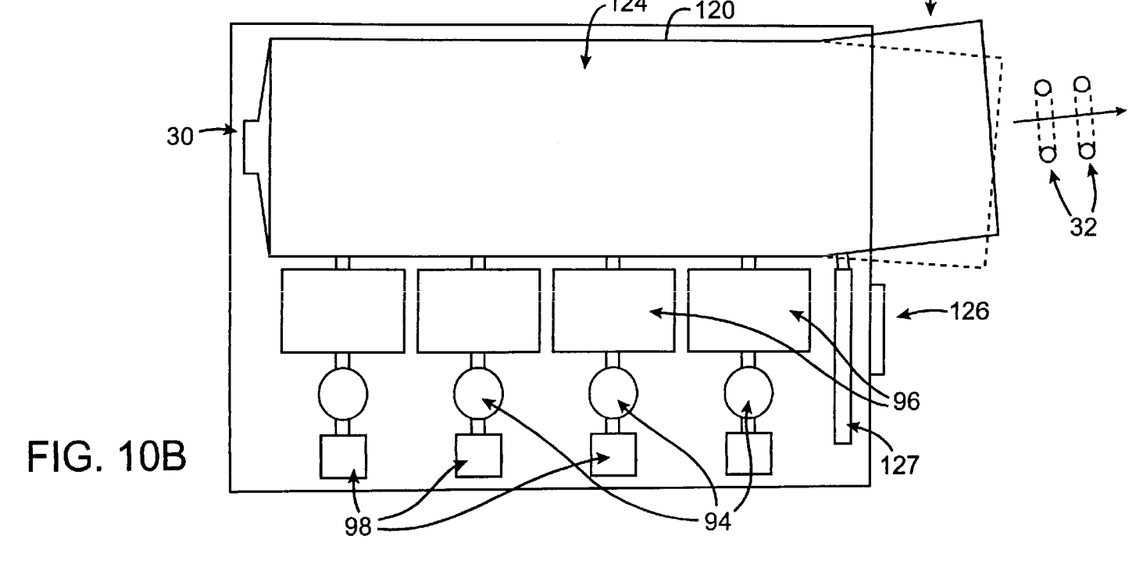
FIG. 10B is an elevational view of the system of FIG. 10A.

In yet other embodiment of the present invention, the delivery assembly 26 can also include at least one of a vaporizer, nano-pump, or micro-pump, to deliver a vapor or aerosol scent chemical to the venting chamber. Formation of an aerosol creates very small, precisely measured droplets of the scent chemical which optimizes the surface area relative to the volume. Optimization of the size of the scent chemical improves the vaporization rate and the dispersion rate of the scent chemical into the atmosphere. Referring now to FIGS. 10A to 10B, one exemplary embodiment includes a micro pump 94 and an ultrasonic spray vaporizer 96. In the embodiment shown, the scent cartridge 22 contains a rubber sleeve 98 that is filled with scent chemicals. Pressure within the cartridge 22 on the rubber sleeve 98 is sufficient to move the scent chemical through a conduit 100 into the micro pump 94. The micro pump 94 produces droplets that are typically in the range of 10 microns to 20 microns. The droplets are moved into the ultrasonic vaporizer 96 where the droplets are vaporized and sprayed into the venting chamber 24. One exemplary micro-metering pump 94 is manufactured by IVEK Corporation, of North Springfield, Vt. As an alternative to the micro pump 94 and vaporizer 96, a nano scale micro miniature pump (not shown) can be attached to the conduit 100 to create smaller measured droplets that do not need to be vaporized.

Figures 11A, 11B, 11C:
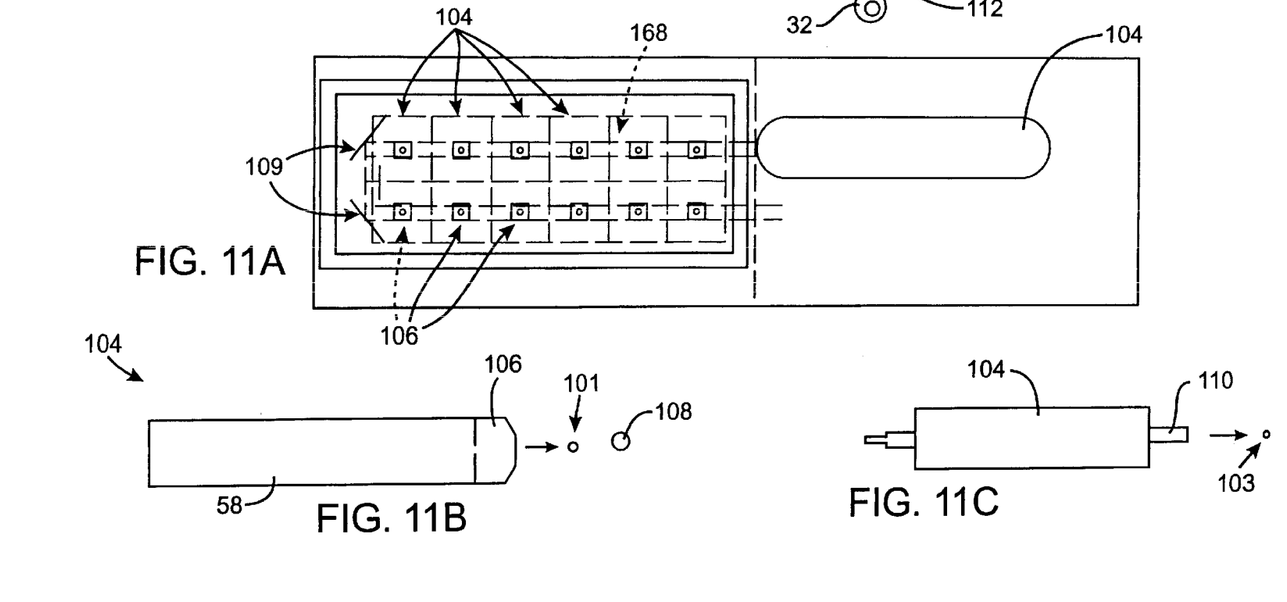
FIG. 11A is a cross sectional view showing the bubble jet ejector cartridges and a laser beam.
FIG. 11B shows a droplet that is ejected from a bubble jet ejector.
FIG. 11C shows a micro valve of the present invention.

Another exemplary delivery system is illustrated in FIGS. 11A and 11B. Because the scent chemical is often a liquid medium, a small concentrated amount of the scent chemical 58 can be expelled in a droplet form 101 from a bubble jet-type cartridge 104. As shown in FIGS. 11A and 11B, the bubble jet cartridges 104 can be placed in rows such that the bubble-jet ejector 106 dispenses the scent chemical 58 into the path of a laser beam 108. A laser 109 generated laser beam 108 passes in front of a row of cartridges and can be reflected by a mirror 109 to pass in front of a second or third row of cartridges. In a specific implementation, the cartridges 104 are approximately 2 inches long and have a cross-sectional size of approximately 0.5 inches×0.5 inches. Accordingly, as many as 60 different scents can be contained in 12 inch×2 inch×4 inch console. One exemplary bubble-jet ejector circuitry and mechanism is manufactured by Hewlett-Packard.

An alternative embodiment to the bubble jet ejector is shown in FIG. 11C. Instead of a bubble jet ejector, a micro valve 110 can be used to deliver the droplet 103 to the laser beam 108. The droplets 103 produced by the micro valve 110 are typically approximately 10 microns. An exemplary micro valve is manufactured by the Lee Company.

Figure 11D:
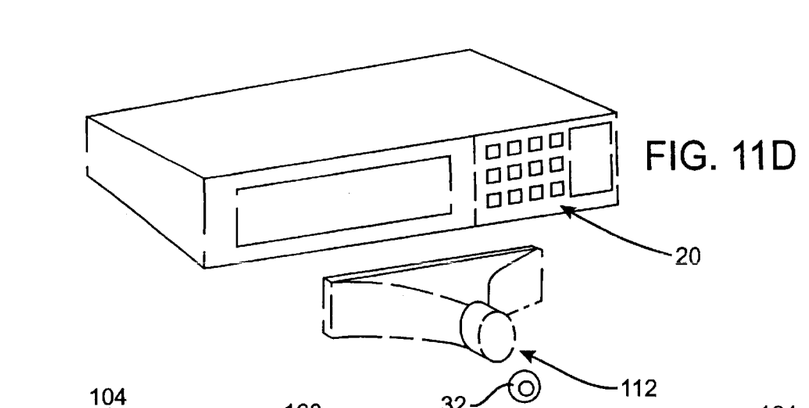
FIG. 11D is a perspective view of a system of the present invention.

In both the bubble jet and micro valve embodiments, the laser beam 108 can vaporize the droplets 103 into a gas 60 or aerosol that is drawn into the venting chamber 24 with an air current. As shown in 11D, a bolus generator (not shown) can be used to direct a bolus ring 32 of scent chemical at the user through the directional spout 112.

Figure 12:
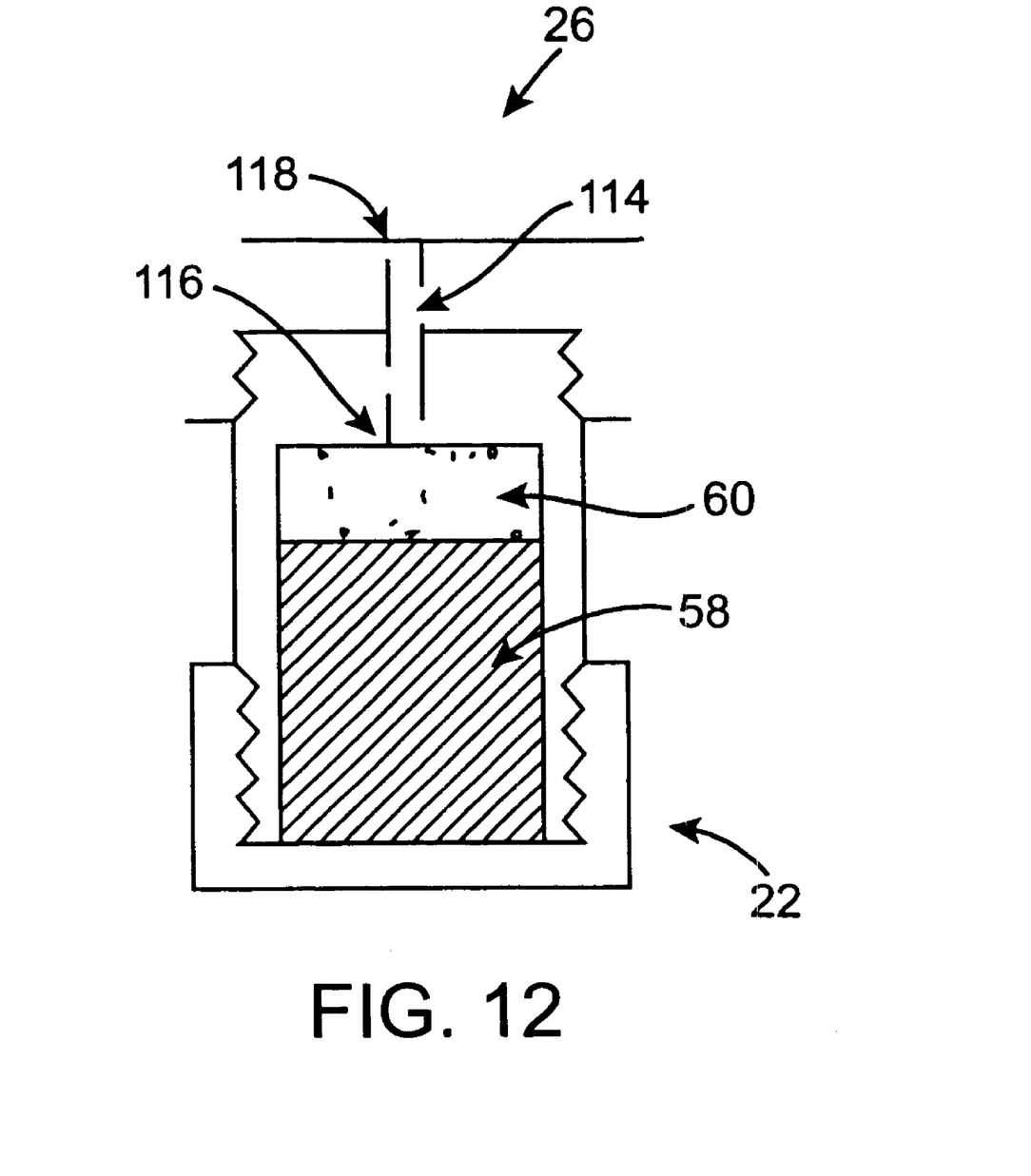
FIG. 12 shows a cartridge having a capillary delivery system.

In still another embodiment, the cartridge 22 can include a delivery assembly 26 having a capillary tube 114 and sealing gates 116, 118. As shown in FIG. 12 the capillary tube 114 having sealing gates 116, 118 on both ends of the tube allow a measured quantity of the scented vapor to be delivered to the venting chamber (not shown). The bottom sealing gate 116 will open to allow a measured amount of scent vapor 60 to enter the capillary tube 114. Once the capillary tube 114 has been filled, the bottom sealing gate 118 is closed. To release the vapor into the venting chamber 24 the top sealing gate 118 is opened. When air is blown over the open end of the capillary tube 114, the measured quantity of scent vapor 60 is then drawn into the venting chamber 24.

Figure 3:
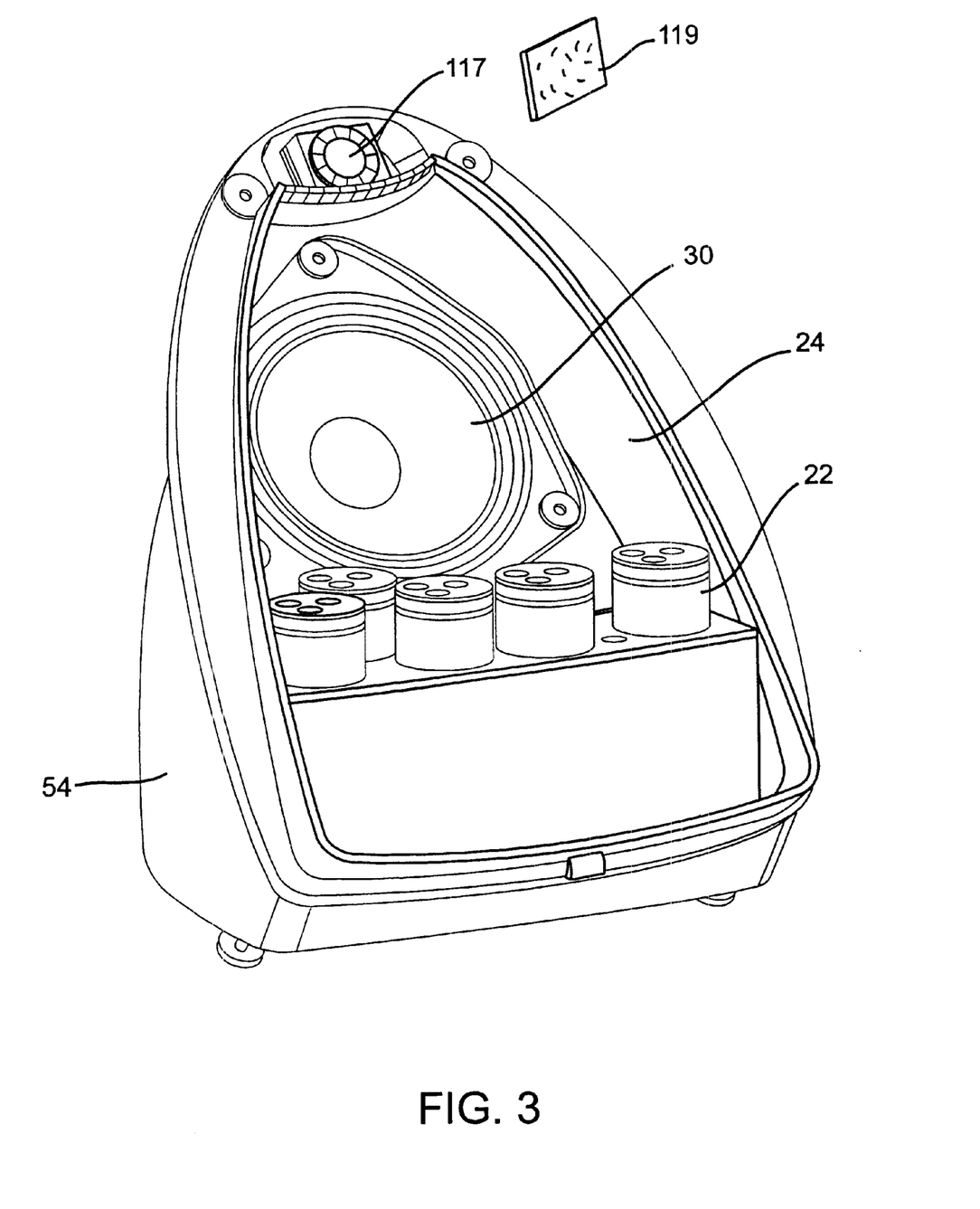
FIG. 3 is an isometric view of the system of FIG. 2 with the front panel removed.
Figure 4:
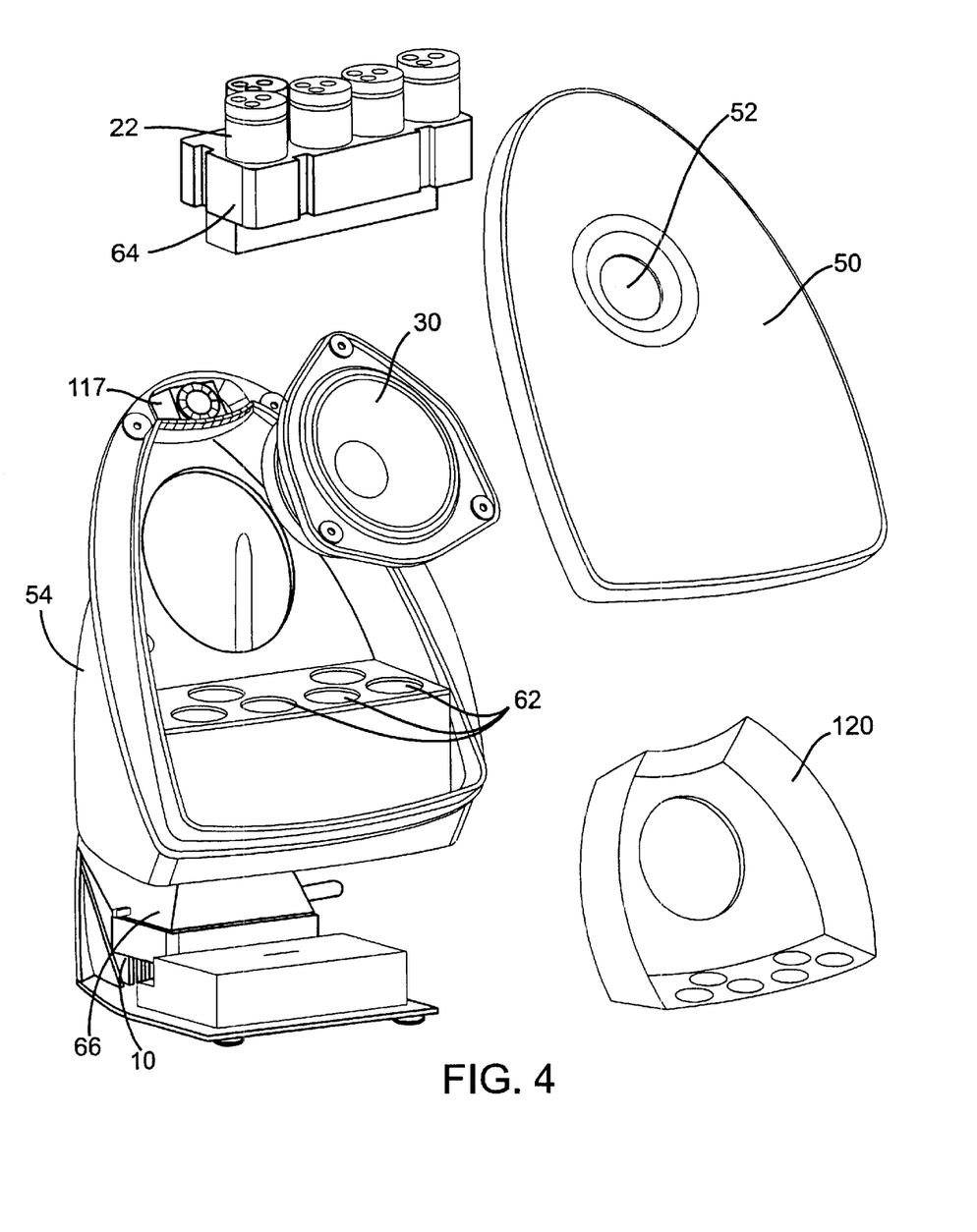
FIG. 4 is an exploded isometric view of the system of FIG. 2.
Figure 5:
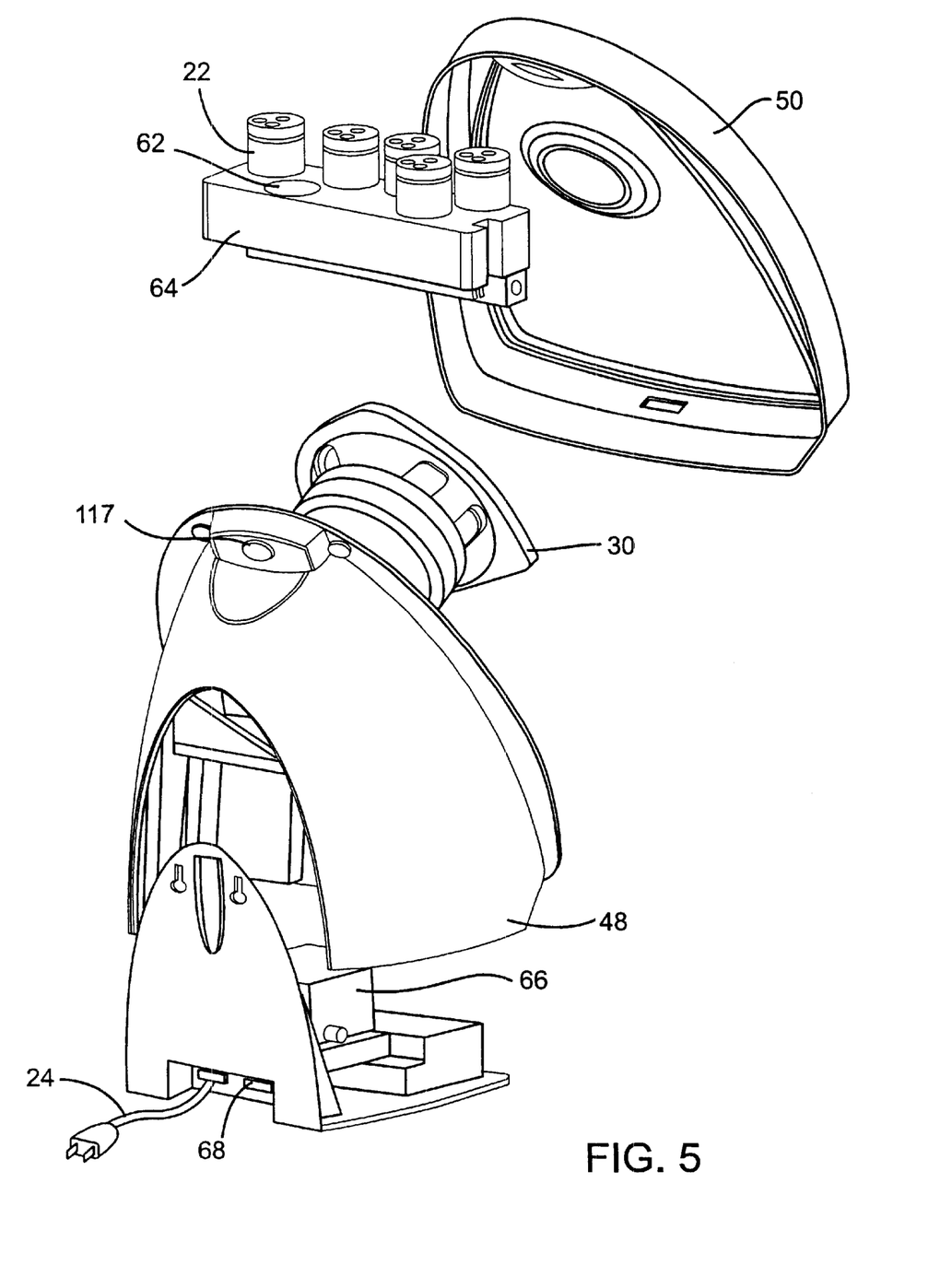
FIG. 5 is an exploded rear isometric view of the system of FIG. 2.

Another aspect of the present invention is the ability to reduce contamination of subsequently delivered scents. In order to reduce scent chemical contamination the venting chamber 24 can be equipped with various anti-contamination means. In one embodiment, the air can be filtered with filter 115 as it is drawn into the venting chamber so as to remove scent chemicals that are in the atmospheric air (FIG. 9C). As shown in FIGS. 3 to 5, the venting chamber can also have an exhaust fan 117 and a filter 119 to remove the lingering air and scent chemicals in the venting chambers. The exhaust fan 117 forces the lingering air through the filter 119 and away from the user.

Optionally, a permanent or removable absorptive liner 120 can be placed within the scent generating system 20, and particularly within the venting chamber 24 to absorb any residue of the scent chemical. The absorptive liner 120 can be made of a chemically treated material that is capable of absorbing at least some of the scent chemicals 58, 60. As shown in FIG. 4, the absorptive liner 120 can be fitted with openings which correspond to the orifice 52, the bolus generator 30 and the cartridges 22. The absorptive liner 120 can be made of any scent absorbing material, such as clay, a wood-clay combination, activated carbon, vermiculite, silica gel, zeolite, activated alumina, Gray Matter™, microsponge, or the like. Naturally, it will be appreciated that the absorptive liner 120 can cover the entire inner wall of the venting chamber or it can only cover a selected portion of the venting chamber. For example, the absorptive liner can be composed of smaller pieces and placed in a variety of other strategic places, such as the conduits.

As an alternative to the absorptive liner, a power supply 122 (FIG. 1) can be used to apply a like electric charge to the inner walls of the venting chamber 24 and to the scented chemical 58, 60. The like charge causes the scent chemicals 58, 60 to be repelled by the venting chamber 24 and limits the adherence of the scent chemical 58, 60 to the inner wall. As shown in FIG. 5, power supply 122 is typically supplied to the scent delivery system 20 through a power cord 124 which attaches to a power outlet at the back of the housing. In addition to creating the electric charge, the power supply 122 can also be used to power the pumps, microprocessor board, bolus generator, and the like (FIG. 1).

Referring again to FIGS. 10A and 10B, some embodiments of the scent generating device will have a directional cylinder 124 at the end of the venting chamber 24 that can be adjusted, either manually or automatically to cause the bolus rings 32 to be aimed at the nose of the user. In the embodiment shown in FIGS. 10A and 10B the automatic aiming mechanism 127, is an electric potentiometer that moves the directional cylinder 124 in response to a signal from a position or motion sensor 126. It will be appreciated however, that the automatic aiming mechanism 127 may move in response to a video imaging camera, an infrared imager a camera, or other means of determining the position of the user and the user's nose.

In addition to using the position or motion sensor 126 to track a person's movement, the motion sensor can be used to simply determine that a person has entered the general vicinity. For example, if the motion sensor 126 senses a person walking near the device associated with the scent generating system, the motion sensor can send a signal to the microprocessor board to deliver a scent to try to "entice" the potential user to approach the video device.

This description of embodiments of the invention is presented for the purposes of illustration and description. It is not intended to be exhaustive or to limit the invention to the precise form described, and many modifications and variations are possible in light of the description above. The embodiments were chosen and described in order to best explain the principles of the invention and its practical applications. This description of embodiments will enable others skilled in the art to best utilize and practice the invention in various embodiments and with various modifications as are suited to the particular use contemplated. It is intended that the scope of the invention be defined by the following claims.

What is claimed is:

1. A method comprising:
   selecting a scent chemical from a plurality of scent chemicals;
   forming an airborne scent ring comprising the scent chemical; and
   directing the scent ring toward a user.

2. The method of claim 1 further comprising metering the scent chemical.

3. The method of claim 1 wherein directing is carried out with a vibratable diaphragm or an audio speaker.

4. The method of claim 1 further comprising transferring the scent chemical from a storage area to a venting area.

5. The method of claim 4 further comprising inhibiting the contamination of the venting area.

6. The method of claim 5 wherein inhibiting comprises absorbing the scent chemicals.

7. The method of claim 5 wherein inhibiting comprises charging the venting area and the scent chemical with the same electrical charge.

8. The method of claim 4 wherein the storage area is a plurality of removable cartridges.

9. The method of claim 8 wherein transferring comprises directing the scent chemical through check valves.

10. The method of claim 4 wherein transferring comprises vaporizing the scent chemical into a gas or an aerosol.

11. The method of claim 10 wherein vaporizing is carried out with a laser.

12. The method of claim 10 wherein vaporizing is carried out with a nano-pump.

13. The method of claim 1 further comprising aiming the scent chemical at a general vicinity of a user's nose.

14. The method of claim 1 wherein selecting comprises choosing more than one scent chemicals.

15. The method of claim 1 further comprising sensing the presence of the user.

16. The method of claim 1 further comprising sensing the location of a user's nose.

17. The method of claim 1 wherein directing comprises limiting disbursement of the scent ring to a localized region.

18. The method of claim 1 wherein directing the scent ring comprises limiting the dispersion of the scent ring such that the scent ring can only be sensed by the user.

19. The method of claim 1 comprising directing the scent ring such that only the user receives the scent ring.

20. The method of claim 1 further comprising adjusting the size of the scent ring.

21. A method comprising:
    selecting a scent chemical from a plurality of scent chemicals;
    forming a bolus comprising the scent chemical and air; and
    directing the bolus toward a user.

22. The method of claim 21 wherein the bolus has a round shape.

23. The method of claim 21 wherein directing is carried out with a vibratable diaphragm or an audio speaker.

24. The method of claim 21 comprising directing the scent ring such that only the user receives the scent ring.

25. A method comprising:
    choosing a scent chemical from a plurality of scent chemicals;
    vaporizing the scent chemical;
    forming, inside a venting chamber, a mixture of the vaporized scent chemical and air;
    venting the mixture from the venting chamber to an atmosphere such that the mixture forms a cohesive unit comprising the air and the vaporized scent chemical; and
    delivering the cohesive unit to a localized region.

26. The method of claim 25 wherein venting is carried out with a vibratable diaphragm or an audio speaker.

27. The method of claim 25 wherein the cohesive unit has the shape of a ring.

28. The method of claim 25 wherein delivering the cohesive unit is carried out such that only the localized region receives the delivery of the cohesive unit.

29. The method of claim 25 wherein the localized region is the general vicinity of a user's face.

* * * * *

UNITED STATES PATENT AND TRADEMARK OFFICE
CERTIFICATE OF CORRECTION

PATENT NO.         : 6,536,746 B2                                            Page 1 of 1
APPLICATION NO.    : 10/000432
DATED              : March 25, 2003
INVENTOR(S)        : Carl J. Watkins et al.

It is certified that error appears in the above-identified patent and that said Letters Patent is hereby corrected as shown below:

On the title page item (75), add

-- CARL J. WATKINS, Eugene, OR (US) and DAVID LAW, Palo Alto, CA (UK) --

Signed and Sealed this

Twenty-ninth Day of August, 2006

JON W. DUDAS
*Director of the United States Patent and Trademark Office*